United States Patent [19]

Papsidero

[11] Patent Number: 5,039,604
[45] Date of Patent: Aug. 13, 1991

[54] TEST DEVICE AND METHOD OF PREPARING SAME, ASSAY KIT AND METHOD FOR THE SIMULTANEOUS DETECTION OF TWO HTLV OR HIV ANTIBODIES

[75] Inventor: Lawrence D. Papsidero, Orchard Park, N.Y.

[73] Assignee: Cellular Products, Inc., Buffalo, N.Y.

[21] Appl. No.: 88,133

[22] Filed: Aug. 21, 1987

[51] Int. Cl.$^5$ ............................................. C01N 33/569
[52] U.S. Cl. ......................................... 435/5; 435/7.1; 435/7.92; 435/974; 435/975; 436/808; 436/809; 422/56; 422/57; 422/58; 422/61
[58] Field of Search ................... 435/5, 7, 810, 7.1, 435/7.92, 974, 975; 422/56, 57, 58, 61; 436/808, 809

[56] References Cited

U.S. PATENT DOCUMENTS 4,315,907  2/1982  Fridlender et al. ................. 435/7.1

FOREIGN PATENT DOCUMENTS 0063810  11/1982  European Pat. Off. ............... 435/7
0173295  3/1986  European Pat. Off. ............... 435/5

OTHER PUBLICATIONS

Lee et al., "Serological Cross-Reactivity Between Envelope Gene Products of Type I and II Human T-Cell Leukemia Virus", Proc. Natl. Acad. Sci., U.S.A., 81(1984), 7579-7583.

Gazzolo et al., "Type-I and Type-III HTLV Antibodies in Hospitalized and Out-Patient Zairians", Int. J. Cancer, 36(1985), 373-378.

Clavel et al., "Molecular Cloning and Polymorphism of the Human Immunodeficiency Virus Type 2", Nature, 324(1986), 691-695.

*Primary Examiner*—Christine Nucker
*Attorney, Agent, or Firm*—Elman & Wilf

[57] ABSTRACT

A kit and method have been developed which can be used to simultaneously detect antibodies to two HTLV or HIV antigens. The kit includes a solid carrier material, such as a microtest plate, having immobilized thereon a mixture of first and second viral antigens. The antigens are from any of HTLV-I, HTLV-II, HIV-I and HIV-II provided, however, that HTLV-II antigen is mixed only with HTLV-I antigen. The kit also comprises labeled-antibodies which are reactive with both the first and second antibodies in a test sample. A biological sample, such as a blood sample, is assayed by contacting it with the immobilized antigens to form reaction products between the immobilized antigens and the antibodies in the sample, followed by contact with the labeled antibodies to form labeled reaction products which can be detected in a suitable manner. The kit and method are useful for rapid screening of biological fluids. Also disclosed herein are a test device having immobilized antigens thereon and a method of preparing that device.

23 Claims, No Drawings

TEST DEVICE AND METHOD OF PREPARING SAME, ASSAY KIT AND METHOD FOR THE SIMULTANEOUS DETECTION OF TWO HTLV OR HIV ANTIBODIES

FIELD OF THE INVENTION

This invention relates to a kit and method useful for the simultaneous detection of a pair of HTLV or HIV antibodies in biological specimens. It also relates to a test device useful in the analytical method and a method of preparing the test device.

BACKGROUND OF THE INVENTION

Human retroviruses, as a family, represent a group of related exogeneous retroviruses which exert a significant proliferative or cytopathic effect upon the target T-lymphocytes they infect. The resulting effects of these retroviruses include T-cell proliferation leukemia, T-cell depletion and immunosuppression in humans infected by the viruses. These retroviruses are known as the HTLV (human T-cell leukemia-lymphoma virus) and HIV (human immuno-deficiency virus) families of T4 tropic retroviruses.

The first human retrovirus discovered, HTLV-I, appears to represent the etiological agent of mature T-cell leukemias and lymphomas as typified by Adult T-cell leukemia. See, for example the investigations reported by Poiesz et al, *Proc. Nat. Acad. Sci. U.S.A.*, 77, 1980 and Yoshida et al, supra, 79, 1982. At present, the presence of HTLV-I and T-cell malignancies are believed to occur at increased rates in the populations of certain Caribbean islands and southern Japan, but HTLV-I is now widely recognized as a worldwide medical concern. People infected with HTLV-I or having come into contact with the virus generally have antibodies directed against HTLV-I in their body fluids, especially in their blood. In addition, a significant portion of the patients suffering from the neurological disorder known as Tropical Spastic Paraparesis possess antibodies to HTLV-I.

Continuing research has determined that there are several additional retroviruses which are of significant medical importance. A third retrovirus isolated and characterized has been variously identified as HTLV-III, Lymphadenopathy Associated Virus (LAV) and AIDS Related Virus. It has been implicated as the etiological agent responsible for Acquired Immune Deficiency Virus (AIDS). See, for example U.S. Pat. No. 4,520,113 (issued May 28, 1985 to Gallo et al). In order to reduce confusion, the scientific community has recently renamed the group of viruses as the Human Immunodeficiency Viruses.

As for other viral diseases, exposure to and infection from any of HTLV or HIV produces an immune response, that is the production of antibodies. More specifically, antibodies to antigens of the viruses have been detected by researchers and clinicians in many sero-epidemiologic studies. The presence of either HTLV-I or HIV-I viral-specific gene sequences in infected cells has also been confirmed using DNA probe technology. Both lines of evidence indicate that transmission of either virus can occur either by vertical or horizontal transmission. Human biological fluids, such as whole blood or components thereof, seminal fluid, saliva, lacrimal fluid and vaginal secretions, are considered as potential vectors for spreading such viruses. Blood samples are particularly likely vectors for virus transmission.

In order to reduce the risk of transmission of HIV-I, all blood banks currently screen blood obtained from all donors for the presence of antibodies against HIV-I. A number of useful screening assays have been developed some of which are described in U.S. Pat. No. 4,520,113 (noted above) and in E.P. Publications 136,798 (Biotech Research) and 216,191 (Abbott). In addition, assays for HTLV-I have been described in E.P. Publications 135,352 (Ajinomoto) and 136,798 (noted above). It is possible that routine screening of blood or other biological fluids for HTLV-I antibodies will also be desired in the future. E.P. Publication 173,295 (N.Y. Blood Center) describes a process for the simultaneous detection of the presence of an antigen and an antibody.

Current technology for testing biological fluids for both HTLV-I and HIV-I antibodies requires the use of two separate tests, one for each viral antibody. This necessitates purchase of two different test kits, possibly from different vendors, and may require different analytical equipment for determination in each test. The use of two separate tests increases testing time as well as purchase and screening costs. In addition, running two separate tests requires a larger sample of the biological fluid and extra handling which can result in procedural error as well as the dangerous possibilitty of contamination of the environment or other materials from spillage or insufficient housekeeping procedures.

It would be highly desirable to be able to routinely screen biological samples, such as blood samples, for pairs of antibodies from the highly infectious HTLV and HIV virus families in an inexpensive, rapid, safe and accurate manner.

SUMMARY OF THE INVENTION

The problems noted above with individual tests for HTLV-I and HIV-I have been overcome with the use of a test device comprising a solid carrier material having immobilized thereon an antibody-free mixture comprising a first viral antigen reactive with a first antibody and a second viral antigen reactive with a second antibody, the first and second viral antigens being from HTLV-I, HTLV-II, HIV-I or HIV-II, provided that when one of the viral antigens is from HTLV-II, the other is from HTLV-I.

This invention also provides an assay kit for the simultaneous detection of first and second antibodies which are antibodies to HTLV-I, HTLV-II, HIV-I or HIV-II, the kit comprising:

(a) a solid carrier material having immobilized thereon an antibody-free mixture comprising a first viral antigen reactive with the first antibody and a second viral antigen reactive with the second antibody, the first and second viral antigens being from HTLV-I, HTLV-II, HIV-I or HIV-II provided that when one of the viral antigens is from HTLV-II, the other viral antigen is from HTLV-I, and (b) labeled antibodies which are reactive with both first and second antibodies.

Additionally, a method for the simultaneous detection of first and second antibodies in a biological sample, the antibodies being to HTLV-I, HTLV-II, HIV-I or HIV-II, comprises:

A. contacting the biological sample with a solid carrier material having immobilized thereon an antibody-free mixture comprising a first viral antigen and a second viral antigen, the antigens being from HTLV-I, HTLV-II, HIV-I or HIV-II provided, that when one of the viral antigens is from HTLV-II, the other viral antigen is from HTLV-I, to form reaction products between the first and second antibodies present in the sample and the immobilized first and second viral antigens, respectively, B. contacting the reaction products with a labeled antibody which is reactive with both first and second antibodies to form labeled reaction products, and C. detecting the presence of the labeled reaction products.

The present invention provides an accurate, rapid and simplified assay for simultaneously detecting the presence of a pair of antibodies against antigens of the HTLV and HIV families. This assay can be advantageously carried out with a single test kit which is described in more detail below. As a result, blood banks and other screening facilities can quickly and accurately test large numbers of biological fluid samples without resort to separate test devices or kits, equipment and screening procedures. It has been found that the assay of the present invention provides high sensitivity and specificity in detecting the pair of antibodies in this single test whereby there are no more false negatives than would be observed when using two individual tests for the antibodies being detected. Although it is important to have minimal false positives, it is critical for safe blood supplies that there be no false negatives in order to avoid severe health hazards.

These advantages were obtained with the present invention by immobilizing an antibody-free mixture of antigens for the antibodies to be determined on a suitable support and allowing an immunological reaction to occur when the test sample and support are contacted. The immobilized mixture of antigens surprisingly does not interfere with the reactivity of either antigen. Contact with an appropriate labeled material (described below) then allows for accurate detection of the presence of either of the pair of antibodies in the test sample.

DETAILED DESCRIPTION OF THE INVENTION

The kit and assay of the present invention can be used to screen a biological sample simultaneously for a pair of antibodies to HTLV and HIV antigens. Biological samples which can be so screened include, but are not limited to, whole blood or a component (serum or plasma) thereof, saliva, lacrimal fluid, spinal fluid, feces, urine, vaginal secretions, seminal fluid, human tissue or organ extracts and human milk. Preferably, the test is used to screen human blood serum or plasma.

The present invention can be used to detect a pair of antibodies simultaneously. For example, antibodies to HTLV-I and HIV-II can be detected simultaneously, as can antibodies to HTLV-I and HTLV-II. HTLV-II can be detected simultaneously only with HTLV-I. In addition, antibodies to HIV-I and HIV-II can be detected as the same time. Preferably, the invention is used to detect antibodies to HTLV-I and HIV-I simultaneously.

The assay of this invention makes use of a test device composed of a solid carrier material having immobilized thereon an antibody-free mixture comprising a first viral antigen and a second viral antigen in the pairs noted above. This antigenic mixture does not contain antibodies. It may contain additional antigens which do not interfere with the assay as well as inert, non-immunologically reactive materials which aid in immobilization or long-term storage.

The HTLV and HIV antigens can be obtained in any suitable manner. They can be naturally occurring viral substances or components thereof, or synthetic peptides, or polypeptides produced using recombinant DNA technology as described, for example, in PCT Publications 86/01834 (University of California, Berkeley) and 86/02930 (Harvard University). Other technical and patent references describing synthetic methods for producing HTLV and HIV antigens are too numerous to mention here.

A preferred manner of obtaining antigens is to culture the virus in a suitable cell line followed by removal of the virus from the cell. The removed virus, or component thereof, is mixed with a second virus, or component thereof, similarly cultured and isolated, and the mixture is immobilized as described below on the solid support for use in the assay. For example, a HTLV-I viral antigen can be obtained by detergent lysis of HTLV-I viral particles isolated from a suitable host cell line. Such cell lines include, but are not limited to Hut 102 and MT-2 and clones thereof. The Hut 102 cell line, which is available from the American Type Culture Collection (ATCC TIB 162), is preferred in preparing HTLV-I antigen for the practice of this invention. HTLV-I may also be isolated from new cell lines established from peripheral blood T-cells or tissues obtained from cutaneous T-cell leukemia/lymphoma patients. Cultivation of the cells and isolation of the viral particles are carried out using known methods. The viral particles can be obtained from multiplied cells and the supernatant by lysis with a suitable surfactant. A detailed cultivation and isolation procedure is outlined below. HTLV-II antigens can be obtained similarly.

As a further example of a source of antigens, a HIV-I viral antigen can be obtained by detergent lysis of HIV-I viral particles isolated from a suitable host cell line. Such cell lines, which are permissive to the growth of HIV-I, include but are not limited to: Hut 78 (ATCC TIB 161), H9 (ATCC No. CRL 8543), Molt 3, CEM, OKT4+, Ti7.4, HT and clones thereof, and others as described, for example, in U.S. Pat. No. 4,647,773 (issued Mar. 3, 1987 to Gallo et al) and U.S. Pat. No. 4,652,599 (issued Mar. 24, 1987 to Gallo et al). Viral particles can also be isolated from new cell lines established from patients having AIDS or what is known as "pre-AIDS" (chronic generalized lymphadenopathy which often precedes AIDS). In addition, antigenic material can be obtained from HIV-infected persons. Cultivation of the cells and isolation of viral particles are carried out using known methods. The viral particles can be obtained from multiplied cells as well as the supernatant by lysis with a detergent or surfactant. The Hut 78 cell line, once infected with HIV-I, is preferred in obtaining HIV-I antigens. HIV-II antigens can be similarly obtained. A detailed cultivation and isolation procedure is outlined below.

The first and second antigens (for example, in individual lysates) are mixed together and immobilized in a suitable fashion on a carrier material. The antigens can be coated, absorbed, covalently attached or in any other manner fixed to the carrier material. In some instances, the antigens are attached through linking or coupling means. For example, one such coupling means is an antibody mixture which is suitably attached to the carrier material and which is reactive for both of the antigens. The antigens can be directly attached by adsorption with or without an inert non-immunologically reactive water-soluble binder material. The immobilized antigen mixture can be stored for an indefinite period of time prior to use if desired. Sufficient amounts of each antigen are immobilized in one or more zones of the carrier material for adequate immunological reaction. Generally, from about 75 to about 500 ng of each viral antigen is immobilized in each reaction zone of the carrier material.

Useful carrier materials include any water-insoluble immunologically non-reactive substance to which the lysate mixture can be attached in some manner. They include, but are not limited to, materials composed of natural or synthetic polymers such as polystyrene, polycarbonates, polyamides, polyolefins (such as polyethylene), and others known in the art, metallic surfaces, metal-impregnated surfaces, silicon materials, and can be in the form of fibers, membranes, test tubes, slides, plates (such as microtest plates), particles and the like. Preferred materials include polymeric plates and beads, such as polystyrene and other polymeric particles and microtest plates having a plurality of surface wells or other surface indentations. The multiwell microtest plate is most preferred in the practice of this invention.

The test device of this invention can be prepared by immobilizing on a carrier material an antibody-free mixture comprising a first viral antigen reactive with a first antibody and a second viral antigen reactive with a second antibody, the first and second viral antigens being from HTLV-I, HTLV-II, HIV-I or HIV-II, provided that when one of the viral antigens is from HTLV-II, the other is from HTLV-I. A general description of this preparatory method is provided above. A detailed description of a preferred embodiment is provided in the Example below.

In addition to the test device described above, an assay kit of this invention can be assembled by combining the test device with labeled antibodies which are reactive with both the first and second antibodies in the test sample. These anti-antibodies can be labeled in any suitable manner which will allow the resulting labeled antigen-antibody-antibody(*) complex to be detected, wherein (*) refers to the label. There is extensive literature describing examples of suitable labels and representative methods of making them. Suffice it to say that such labels include, but are not limited to, enzymes, radioisotopes, detectable particles (such as magnetic particles, colored beads or clear beads which can be detected by light scattering techniques, metallic particles or particulate carbon), chemiluminescent compounds, chromogens, fluorogens, rare earth europium chelates, phosphorescent compounds and others known to one skilled in the art.

In a preferred embodiment, the label is an enzyme. Enzyme labeled-antibodies can be prepared using known techniques or purchased from a number of commercial sources. The enzyme label can be selected from the following representative enzymes: alkaline phosphatase, glucose oxidase, peroxidase, urease and $\beta$-galactosidase. Alkaline phosphatase is preferred in the practice of this invention. The enzyme is conjugated with a suitable polyclonal or monoclonal antibody such as goat antihuman IgG or any other xenobiotic antibody directed against human immunoglobulins or their peptide chains.

Optionally, but preferably, the kit of this invention also comprises one or more control solutions for confirming the accuracy of the assay. For example, it can contain a negative control solution which has been shown by Western blotting to be non-reactive with antibodies to the first and second viral antigens immobilized on the test device. Generally, this solution is obtained from individuals which are seronegative for the immobilized antigens. For example, in a test for HTLV-I and HIV-I antibodies, this solution is composed of human serum obtained from HTLV-I and HIV-I seronegative individuals. The solution can be used diluted or undiluted, but preferably in diluted form.

One or more positive control solutions can also be included in the kit. A first control solution can contain antibodies which are reactive only with the first immobilized antigen, for example, a HTLV-I antigen. This solution is generally composed of human serum obtained from individuals having a high titer of antibody to the first antigen (for example, high-titered HTLV-I seropositive individuals), and has antibody specificaties to major viral antigenic components of the antigen as demonstrated by Western blotting. The solution may be diluted prior to use.

A second control solution is similar to the first control solution except that it contains antibodies reactive with the second viral antigen only.

When the label used in the assay is an enzyme, a color-providing composition may be needed in order to provide a detectable colored species from enzymatic activity. The specific components of the this composition will, of course, depend upon the particular enzyme used in the kit. There is significant patent and other literature which describe the materials needed for a given enzyme. The composition must contain a substrate for the enzyme as well as suitable reagents which react in some manner to provide a colored species. These reagents can react directly with the enzyme and substrate to provide a colored species, or through a series of reactions after enzymatic reaction. The substrate can be the same as or different than the color-providing materials.

For example, if peroxidase is the label, the color-providing composition can include hydrogen peroxide as a substrate and any of monoamines, diamines, phenols, polyphenols, aromatic acids, leuco dyes and other materials which provide a colored species in the presence of oxidized hydrogen peroxide. Similar substrates and color-providing materials are known for glucose oxidase, urease, and the other enzymes noted above.

In a preferred embodiment, the enzyme label is alkaline phosphatase. A number of color-providing compositions for this enzyme are known which also act as substrates including the preferred p-nitrophenyl phosphate which is catalyzed to form the colored species p-nitrophenol and free phosphate. Other alkaline phosphatase substrates include organic monoor diesters of phosphoric acid or a salt thereof, including but not limited to, phenolphthalein monophosphate, phenolphthalein diphosphate, thymolphthalein monophosphate, indoxyl phosphate, phenyl phosphate $\alpha$-nathphol phosphate, $\beta$-glycerol phosphate, $\beta$-naphthol phosphate, o-carboxyphenyl phosphate, o-methylfluorescein phosphate, alkali metal or ammonium salts thereof and others known in the art (for example, U.S. Pat. No. 3,425,912).

Other optional components of the test kit of this invention include buffers, diluents (such as for diluting the test sample, conjugate solution, control solutions or substrate), wash fluids and stop solutions for stopping enzymatic reaction. These materials would be obvious to one skilled in the art. Specific materials are illustrated in the Example below.

In one embodiment of this invention, a method for the simultaneous detection of first and second antibodies in a biological sample, the antibodies being to HTLV-I, HTLV-II, HIV-I or HIV-II, comprises:

A. contacting the biological sample with a solid carrier material having immobilized thereon an antibody-free mixture comprising a first viral antigen and a second viral antigen, the antigens being from HTLV-I, HTLV-II, HIV-I or HIV-II, provided that when one of the viral antigens is from HTLV-II the other viral antigen is from HTLV-I, to form reaction products between the first and second antibodies present in the sample and the immobilized first and second viral antigens, respectively, B. simultaneously with or subsequently to contacting step A, contacting the antigen mixture with predetermined amounts of the first and second antibodies which are labeled to form reaction products between the labeled first and second antibodies and the immobilized first and second viral antigens, and C. measuring the amount of labeled reaction products as a indication of the amount of the first and second antibodies in the biological sample.

This embodiment is generally known in the art as a competitive binding assay. In such an assay, the immobilized antigens are contacted with corresponding labeled first and second antibodies in predetermined quantities. The label can be any suitable label as described above. These labeled antibodies are reactive with the first and second immobilized antigens, and compete for the antigenic sites with any first and second antibodies in the test sample. As is known in the art, the labeled antibodies are generally added simultaneously with the test sample, although addition of labeled antibodies subsequent to it is also possible. In the competitive binding reactions, both labeled and unlabeled reaction products are formed and are separated in a suitable manner if separation is necessary for detection (separation may not be necessary in what are known as homogeneous assays as opposed to heterogeneous assays). The labeled reaction products are then detected in a suitable manner to indicate the amount of first and second antibodies in the test sample.

A preferred embodiment of this invention is a method known in the art as an ELISA test whereby two analytes (herein, a pair of HTLV or HIV antibodies) are complexed with two immobilized receptors (that is, molecules which complex specifically with the analytes), and the resulting reaction complexes are detected by addition of a labeled antibody reactive with the reaction complex (that is, the antibodies of the test sample).

More specifically, the first step in detecting the antibodies is to contact a biological fluid sample with the immobilized corresponding antigens as described above. The contact can be accomplished in any suitable manner, including immersing the carrier material in a test sample, or by adding test sample to the carrier material, for example, a few drops. Preferably, from about 50 to about 250 microliters of the diluted sample are applied to individual zones of the carrier material (for example, wells of the microtest plate) to form immobilized antibody-antigen reaction products. It should be understood that the method of this invention will detect if either or both of the first and second antibodies are in the biological sample.

The formation of the reaction products can be facilitated if desired by incubation at from about 20° to about 45° C. for up to 120 minutes. If desired, unreacted materials can be removed from reacted materials in a suitable manner, such as with buffered wash solutions or aspiration.

Once the reaction products have been formed, they are contacted with a suitable labeled-antibody conjugate. The antibody of the conjugate reacts with both of the first and second antibodies in the immobilized reaction products. Again, suitable incubation may facilitate this complexation, and uncomplexed materials can be removed from the complexed materials by washing or otherwise.

At this point in the assay, the labeled antigen-antibody-antibody(*) reaction products are detected using the appropriate detection procedures and equipment. In a preferred embodiment where the label is an enzyme, an appropriate color-providing composition containing an enzyme substrate and any other color-providing reagents is added to generate a detectable colored species. This species is then observed with the unaided eye or suitable spectrophotometric equipment.

The following example is not meant to be limiting, but shows a representative test device, kit and method of the present invention. It also shows a representative method for preparing the test device. The following preparatory methods were followed.

PREPARATION OF HIV-I ANTIGEN

HIV-I was cultured in the Hut 78 cell line in Roswell Park Memorial Institute-1640 medium with 10% fetal bovine serum and 50 $\mu$g/ml gentamycin. The cultures were maintained at 37° C. in an incubator. The cell density was maintained at approximately $1\times10^5$ to $1\times10^6$ cells/ml, and the cells were subcultured by the addition of fresh medium to maintain this density. The viral particles were isolated in a closed-system stainless steel filtration/concentration apparatus by pooling the cultures to be harvested in a holding tank which permits the cell culture fluid to be pumped through a filter housing fitted with a 0.45 $\mu$m filter. This first filtration step removed whole cells and cell debris. The cell-free supernatant was then pumped through a second filter housing fitted with a 0.2 $\mu$m filter in order to eliminate any residual cell debris not removed by the 0.45 $\mu$m filter. The second supernatant was pumped through a concentration cassette fitted with a 100,000 dalton cut-off membrane to concentrate the preparation to a suitable volume. The crude viral particles thus obtained were pelletized by centrifugation for two hours at about 50,000$\times$g and resuspended in about 40 ml of a buffer solution [pH 7.8, 0.01 molar tris(hydroxymethyl)aminomethane hydrochloride, 0.01 molar NaCl, 0.001 molar ethylenediaminetetraacetic acid] layered over a 1300 ml linear 22–65% sucrose gradient in the buffer with a conventional zonal rotor and ultracentrifuged overnight at about 30,000$\times$g. The gradient was fractionated into about 110 fractions (12 ml each) and all fractions with densities between 1.14 and 1.18 g/ml were pooled, diluted 3- to 4-fold with the buffer and centrifuged at about 50,000$\times$g for two hours to recover the purified HIV-I viral particles. The particles were then suspended in 10 ml of a solution containing 0.6 molar KCl and 0.5% of a nonionic octylphenoxy polyethoxyethanol surfactant, sonicated with three 5-second bursts, incubated for one hour at 37° C. and centrifuged at 80,000$\times$g for one hour to remove debris. The solubilized HIV-I preparation was then extracted twice with an equal volume of anhydrous ether and the resulting aqueous phase was used as the source of HIV-I antigen in the antigenic mixture used in the following example.

PREPARATION OF HTLV-I LYSATE

HTLV-I was cultured in the Hut 102.B.2 cell line and isolated in a similar fashion as HIV-I except that the purified viral particles were not sonicated as part of the disruption process. The Hut 102.B.2 cell line is a subclone of Hut 102 which is available from ATCC. The sub-clone is described by Poiesz et al, *Cancer Cells*, 3, pp. 237–245 (1983).

EXAMPLE

The following kit components were provided and used to detect HTLV-I and HIV-I antibodies in blood serum samples in the assay described below.

KIT COMPONENTS

1) A test device composed of a standard microtest plate (96 wells) coated with a mixture of HTLV-I viral antigen and HIV-I viral antigen prepared as described above. The antigens were adsorbed onto the plate by incubating the antigenic mixture at room temperature for about 18 hours. Coating was accomplished in all of the wells of the microtest plate. The quantity of each viral antigen in each well was about 150 ng.

2) A negative control solution composed of human serum obtained from HTLV-I and HIV-I seronegative individuals and 0.05% thimerosal preservative. Before use, this solution was diluted 1:21 with the sample diluent (described below) to yield absorbance readings at 405 nm between 0.0 and 0.2 when the assay is performed as described herein. Appropriate wells of the microtest plate were coated with the diluted negative control solution.

3) A HTLV-I positive control solution composed of human serum obtained from high-titered HTLV-I seropositive individuals and 0.05% thimerosal preservative. Before use, this solution was standardized against an in-house standard (prepared according to conventional techniques) and diluted 1:21 with the sample diluent to yield absorbance readings at 405 nm between 0.35 and 1.35. Appropriate wells of the microtest plate were coated with this positive control solution.

4) A HIV-I positive control solution composed of human serum obtained from high-titered HIV-I seropositive individuals and 0.05% thimerosal preservative. Before use, this solution was standardized against an in-house standard (prepared using conventional techniques) and diluted 1:21 with the sample diluent to yield an absorbance reading at 405 nm between 0.35 and 1.35. Appropriate wells of the microtest plate were coated with this positive control solution.

5) Sample diluent composed of phosphate buffered saline solution (pH 7.3), 20% heat-inactivated goat serum, 0.05% polyoxyethylenesorbitan surfactant, 1% bovine serum albumin, 0.005% thimerosal and 0.1% sodium azide preservatives. This diluent was used to dilute the test sample, control solutions and enzyme-antibody conjugate solution.

6) Lyophilized conjugate of alkaline phosphatase and goat antihuman IgG (heavy and light chain specific), purchased from Jackson Immunoresearch Labs, Inc. (Avondale, Pa.). Before use, the conjugate was rehydrated with 1 ml of the sample diluent, and further diluted 1:500 with additional diluent.

7) Solid p-nitrophenyl phosphate substrate tablets (5 mg) which were purchased from Sigma Chemical Co. (St. Louis, Mo.). A substrate solution was prepared a few minutes prior to use using the diluent described below.

8) A diluent for the substrate composed of 0.5 mmolar magnesium chloride and 0.1% sodium azide preservative in 1 molar diethanolamine.

9) Washing buffer for washing the plate when needed is composed of phosphate buffered saline containing 0.05% polyoxyethylenesorbitan surfactant and 0.1% chloracetamide preservative.

10) Enzyme reaction stop solution to terminate reaction of alkaline phosphatase prior to reading the color in each well at 405 nm was composed of 3 normal sodium hydroxide.

The kit described above was used to detect HTLV-I and HIV-I antibodies in human blood serum samples in the following manner:

All test components were allowed to warm to room temperature and the appropriate solutions were diluted as noted above. Using a micropipettor adjusted to 200 μl, four wells of the microtest plate were filled with the HTLV-I positive control solution, and four wells were likewise filled with the HIV-I positive control solution. Two different wells were filled with the negative control solution (200 μl each). A test sample (200 μl) was placed into a single different well of the plate. Still another well was filled only with a sample of the sample diluent (200 μl).

The coated plate was then covered and incubated at 37° C. for about 45 minutes, followed by aspiration of the contents of each well. Each well was then washed six times with the washing buffer noted above and dried by aspiration.

To each well was added the diluted enzyme-labeled antibody conjugate solution (200 μl), and the plate was again covered and incubated at 37° C. for about 45 minutes. The contents of the wells were aspirated, and the wells were again washed six times with the washing buffer. Reconstituted substrate (200 μl) was added to each well, and the plate was covered and incubated at 37° C. for about 30 minutes. The enzymatic reaction was stopped with the addition of 50 μl of stop solution to each well.

The absorbance of each well was read within 60 minutes of stopping the enzymatic reaction using a conventional ELISA plate reader equipped with a 405 nm filter. This reader was programmed to make all absorbance readings against that of the blank well.

The results of the tests were calculated in the following manner. The two negative control well readings were added together and divided by two to obtain an average absorbance which should read between 0 and 0.20 (optical density) after substracting the blank well absorbance. A mean absorbance was calculated for each of the HTLV-I and HIV-I positive control readings. To calculate a mean, at least three of the four readings must be in the range of 0.35 and 1.35 O.D. after blank subtraction. If more than one reading for each of the HTLV-I and HIV-I positive controls is outside the range, the assay must be repeated. In addition, the readings used in calculating the mean must be within 30% of the calculated mean absorbance.

A cutoff absorbance value for the positive controls was calculated by dividing the lowest mean absorbance of the controls by two. A sample/cutoff value (S/C) was calculated by dividing the test sample absorbance by the cutoff absorbance value. This value is considered the cutoff value between non-reactive and reactive readings. Assays giving an S/C value less than one are considered "negative". Assays giving a S/C value greater than or equal to 1 were repeated twice using the same test sample. When both duplicate tests gave a S/C value less than 1, the test was considered non-reactive, and as giving a "negative" value for that test sample. If one or both of the duplicate tests give a S/C value greater than or equal to 1, the test was considered "positive".

The test samples were also tested for the presence of HTLV-I and HIV-I antibodies individually using commercially available HTLV-I and HIV-I ELISA assays (available from Eastman Kodak Co., Rochester, N.Y.) which detect the presence of only one of the antibodies per test.

The results of the tests made according to the present invention as well as using the individual control assays are shown in Table I below with explanation of the results following.

TABLE I

| Test Samples | Number of Positive Results | | | No. of False Positives[a] (Invention) | No. of False Negatives[b] (Invention) |
|---|---|---|---|---|---|
| | HTLV-I Alone | HIV-I Alone | Invention (HTLV-I/HIV-I) | | |
| Normal Donors* | 0 | 0 | 0 | 0 | 0 |
| ATL Patients** | 22 | 1[c] | 22 | 0 | 0 |
| AIDS/ARC Patients*** | 0 | 40 | 40 | 0 | 0 |
| High Risk Patients@ | 8 | 2 | 10 | 1[d] | 0 |
| Carcinoma Patients# | 0 | 0 | 0 | 0 | 0 |
| Patients With Other Viral Infections$ | 0 | 0 | 0 | 0 | 0 |

In Table I, the Test Samples were obtained as follows:

* 109 blood serum samples obtained from normal blood donors through a local blood bank and Dr. Bernard Poiesz of the Upstate Medical Center (Syracuse, N.Y.), which samples tested negative for HTLV-I and HIV-I in both the individual control assays and the assay of this invention.

** 22 blood serum samples obtained through Dr. Poiesz or Toyobo Co. Ltd. (Japan) from patients known to have adult cell leukemia.

*** 40 blood serum samples obtained from patients diagnosed to have AIDS or "pre-AIDS".

@ 10 blood serum samples obtained from patients considered high-risk for infection for HTLV-I or HIV-I, for example, intravenous drug abusers, relatives of known infected patients, those with myelopathy, etc.

7 blood serum samples obtained from cancer patients.

$ 27 blood serum samples obtained from patients infected with various viruses, for example hepatitis, measles, rubella, parainfluenza, Epstein barr virus, varicella zoster virus and cytomegalovirus.

Note (a) A false positive is defined as the occurrence of an HTLV-I/HIV-I positive S/C value when the individual control assays show a negative value.

Note (b) A false negative is defined as the occurrence of an HTLV-I/HIV-I negative S/C value when the individual control assays show a positive value for either viral antibody.

Note (c) This positive was confirmed by HIV-I Western blot.

Note (d) This sample was from an intravenous drug abuser which gave the following control S/C values: 0.89 for HTLV-I and 0.61 HIV-I.

It is apparent from the test results in Table I that the present invention provides a highly sensitive and specific test for simultaneous detection of a pair of antibodies, for example, HTLV-I and HIV-I antibodies.

The invention has been described in detail with particular reference to preferred embodiments thereof, but it will be understood that variations and modifications can be effected within the spirit and scope of the invention.

I claim:

1. A test device comprising a solid carrier material having immobilized thereon an antibody-free admixture comprising a first viral antigen reactive with a first antibody and a second viral antigen reactive with a second antibody, said first viral antigen being from HTLV-I and said second viral antigen being from HIV-I, provided that no antibody-reactive antigen that is not from HTLV-I or HIV-I is immobilized on said solid carrier material and provided that no antibody is immobilized on said carrier material.

2. The test device of claim 1 wherein said carrier material is a microtest plate.

3. An assay kit for the simultaneous detection of first and second antibodies which are antibodies to HTLV-I or HIV-I, said kit comprising:

a solid carrier material having immobilized thereon an antibody-free admixture comprising a first viral antigen reactive with said first antibody and a second viral antigen reactive with said second antibody, said first viral antigen being from HTLV-I and said second viral antigen being from HIV-I, provided that no antibody-reactive antigen that is not from HTLV-I or HIV-I is immobilized on said solid carrier material and provided that no antibody is immobilized on said carrier material, and labeled antibodies which are reactive with both first and second antibodies.

4. The assay kit of claim 2 further comprising one or more positive or negative control solutions.

5. The assay kit of claim 2 wherein said labeled antibodies are labeled with a detectable species selected from the group consisting of enzymes, radioisotopes, detectable particles, chemiluminescent compounds, chromogens, fluorogens and phosphorescent compounds.

6. An assay kit for the simultaneous detection of first and second antibodies which are antibodies to HTLV-I or HIV-I, said kit comprising:

(a) a solid carrier material having immobilized thereon an antibody-free admixture comprising a first viral antigen reactive with said first antibody and a second viral antigen reactive with said second antibody, said first viral antigen being from HTLV-I and said second viral antigen being from HIV-I, provided that no antibody-reactive antigen that is not from HTLV-I or HIV-I is immobilized on said solid carrier material and provided that no antibody is immobilized on said carrier material, and (b) a negative control solution which is non-reactive with antibodies against either first and second viral antigens, (c) a positive control solution comprising antibodies reactive with said first viral antigen, (d) a positive control solution comprising antibodies reactive with said second viral antigen, and (e) a sample of labeled antibodies which are reactive with both first and second antibodies.

7. The kit of claim 6 wherein said labeled antibodies comprise an enzyme label and said kit further comprises a color-providing composition for said enzyme.

8. The kit of claim 7 wherein said enzyme is alkaline phosphatase, and said color-providing composition comprises a substrate for alkaline phosphatase.

9. The kit of claim 8 wherein said substrate is p-nitrophenylphosphate.

10. The kit of claim 6 wherein said first and second viral antigens are present in a mixture of lysates obtained from virus producing cells.

11. The kit of claim 6 wherein said solid carrier material is a microtest plate.

12. A method for the simultaneous detection of first and second antibodies in a biological sample, said antibodies being to HTLV-I or HIV-I, said method comprising:

A. contacting said biological sample with a solid carrier material having immobilized thereon an antibody-free admixture comprising a first viral antigen and a second viral antigen, said antigens being from HTLV-I or HIV-I, provided that no antibody-reactive antigen that is not from HTLV-I or HIV-I is immobilized on said solid carrier material and provided that no antibody is immobilized on said carrier material, to form reaction products between said first and second antibodies present in said sample and said immobilized first and second viral antigens, respectively, B. contacting said reaction products with a labeled antibody which is reactive with both first and second antibodies to form labeled reaction products, and C. detecting the presence of said labeled reaction products.

13. The method of claim 11 wherein said biological sample is human whole blood or a component thereof.

14. The method of claim 12 wherein said labeled antibodies comprise an enzyme label, and said labeled reaction products are detected with a color-providing composition for said enzyme.

15. The method of claim 14 wherein said enzyme is alkaline phosphatase, and said color-providing composition comprises a substrate for alkaline phosphatase.

16. A method for the simultaneous detection of the presence of antibodies to either HTLV-I or HIV-I antigens in a sample of human whole blood or a component thereof, said method comprising:

A. contacting said biological sample with a microtiter plate having immobilized thereon an antibody-free admixture comprising disrupted HTLV-I viral antigen and disrupted HIV-I viral antigen, to form reaction products between HTLV-I and HIV-I antibodies present in said sample and said immobilized HTLV-I and HIV-I antigens, respectively, B. contacting said reaction products with an enzyme-labeled antibody which is reactive with both HTLV-I and HIV-I antibodies in said reaction products, C. adding a composition comprising a substrate for said enzyme to provide a colored species as a result of the presence of either HTLV-I or HIV-I antibodies, and D. detecting said colored species, provided that no antibody-reactive antigen that is not from HTLV-I or HIV-I is immobilized on said microtiter plate and provided that no antibody is immobilized on said microtiter plate.

17. A method for the simultaneous detection of first and second antibodies in a biological sample, said antibodies being to HTLV-I or HIV-I, said method comprising:

A. contacting said biological sample with a solid carrier material having immobilized thereon an antibody-free admixture comprising a first viral antigen and a second viral antigen, said first viral antigen being from HTLV-I and said second viral antigen being from HIV-I, to form reaction products between said first and second antibodies present in said sample and said immobilized first and second viral antigens, respectively, B. simultaneously with or subsequently to said contacting step A, contacting said antigen admixture with predetermined amounts of said first and second antibodies which are labeled to form reaction products between said labeled first and second antibodies and said immobilized first and second viral antigens, and C. measuring the amount of labeled reaction products as an indication of the amount of said first and second antibodies in said biological sample, provided that no antibody-reactive antigen that is not from HTLV-I or HIV-I is immobilized on said solid carrier material and provided that no antibody is immobilized on said carrier material.

18. A method for the preparation of a test device comprising immobilizing on a solid carrier material an antibody-free admixture comprising a first viral antigen reactive with a first antibody and a second viral antigen reactive with a second antibody, said first viral antigen being from HTLV-I and said second viral antigen being from HIV-I, provided that no antibody reactive-antigen that is not from HTLV-I of HIV-I is immobilized on said solid carrier material and provided that no antibody is immobilized on said carrier material.

19. The method of claim 18 wherein said first antigen is HTLV-I viral antigen obtained from Hut 102 cells or a clone thereof.

20. The method of claim 18 wherein said second antigen is HIV-I viral antigen obtained from HIV-I infected Hut 78 cells.

21. The method of claim 18 wherein said carrier material is a microtest plate.

22. The method of claim 18 wherein said first and second antigens are immobilized on said carrier material by adsorption.

23. The method of claim 18 wherein said first and second antigens are immobilized on said carrier material with an unlabeled antibody reactive with said antigens.

* * * * *

UNITED STATES PATENT AND TRADEMARK OFFICE
CERTIFICATE OF CORRECTION

PATENT NO. : 5,039,604

DATED : August 13, 1991

INVENTOR(S) : Lawrence D. Papsidero

It is certified that error appears in the above-identified patent and that said Letters Patent is hereby corrected as shown below:

Column 12, line 50, "2" should be "3";

Column 12, line 52, "2" should be "3"; and

Column 13, line 50, "11" should be "12".

Signed and Sealed this

Tenth Day of August, 1993

Attest:

MICHAEL K. KIRK

Attesting Officer

Acting Commissioner of Patents and Trademarks